United States Patent
Kharazmi et al.

[11] Patent Number: 6,024,960
[45] Date of Patent: Feb. 15, 2000

[54] ROSE-HIP FORMULATIONS AS ANTI-INFLAMMATORY NATURAL MEDICINE FOR ALLEVIATING/REDUCING SYMPTOMS ASSOCIATED WITH INFLAMMATION AND ARTHRITIS

[75] Inventors: Arsalan Kharazmi, Hellerup; Kaj Winther; Eydbjørg Rein, both of Randbøl, all of Denmark

[73] Assignee: Otto Torbjorn Hansen and Marianne Hansen, Tullebolle, Denmark

[21] Appl. No.: 09/061,969

[22] Filed: Apr. 17, 1998

[51] Int. Cl.[7] .................................................. A61K 35/78
[52] U.S. Cl. ...................... 424/195.1; 514/825; 426/655
[58] Field of Search ........................ 424/195.1; 426/655

[56] References Cited

U.S. PATENT DOCUMENTS

| | | | |
|---|---|---|---|
| 4,774,229 | 9/1988 | Jordan | 514/25 |
| 5,744,187 | 4/1998 | Gaynor | 426/599 |

FOREIGN PATENT DOCUMENTS

086162A1  2/1998  European Pat. Off. .

OTHER PUBLICATIONS

CA104: 174649 F. Morishige Nissan Chem. Ind. Ltd. Japan Dec. 11, 1985.

CA 101:136 B. Spilker et al 1984 (35)(4) 593–605.

Fabad.J.Pharm. Sci. 15, 121–131, 1990 S.Kurucu et al.

*Primary Examiner*—Peter F. Kulkosky
*Attorney, Agent, or Firm*—Nims, Howes, Collison Hansen & Lackert

[57] ABSTRACT

A formulation having a rose hip concentrate is used to treat and/or alleviate the symptoms associated with inflammation including arthritis or to prevent development of arthritis. The rose hip concentrate has a high vitamin content relative to conventionally dried material, and is shown, in vitro, to inhibit the chemotaxis and oxidative burst response of human peripheral blood inflammatory cells, as well as the chemotaxis of monocytes. The formulation, in vivo, was found to inhibit chemotaxis of human peripheral blood inflammatory cells and to reduce the level of C-reactive protein, to alleviate pain and reduce inflammation in patients with arthritis.

22 Claims, 4 Drawing Sheets

ROSE-HIP FORMULATIONS AS ANTI-INFLAMMATORY NATURAL MEDICINE FOR ALLEVIATING/REDUCING SYMPTOMS ASSOCIATED WITH INFLAMMATION AND ARTHRITIS

FIELD OF THE INVENTION

The present invention relates to the use of dried rose-hip for the preparation of formulations for the treatment or prophylaxis of a number of conditions associated with inflammation including arthritis. The invention also relates to methods of preparing these formulations.

BACKGROUND OF THE INVENTION

Inflammatory diseases such as arthritis involve a broad spectrum of different clinical manifestations. The most well known and best studied form of arthritis is rheumatoid arthritis (RA). A number of general principles apply to the pathogenesis of arthritis: 1) different cell types such as polymorphonuclear leukocytes, monocyte/macrophages and T-cells are involved and that these cells interact with each other in this disease; 2) inflammatory cytokines such as tumor necrosis alpha (TNF$\alpha$), interleukine-I (IL-1) and interleukine-6 (IL-6) control and amplify the inflammatory cycles at many points of the evolution of the disease; 3) other biological pathways are down- or up-regulated during inflammation; and 4) spontaneous remissions are not infrequent in some forms of arthritis such as RA. This may mean that minor adjustments in regulatory factors that activate or suppress the arthritic process are sufficient to dampen the entire process, resulting in control of the immune response and suppression of inflammation and tissue damage. Based on the principles involved in the pathogenesis of arthritis one can conclude that, a truly effective remission inducing therapy for arthritis probably will not necessarily involve a cytotoxic drug or a potent immunosuppressive drug but rather a less harmful preferably natural product that, if introduced or applied in the right manner to the patient, can trigger a healing process and prevent disease progression.

Incidence of arthritis appears to be approximately the same in most populations throughout the world, about 1% of adult females and 0.5% of adult males. Some pockets of higher incidence has been observed in certain parts of the world. However, the role of sex appears to be stronger than any geographical or racial factors as a disease determinant. It is claimed that in the Western World approximately 70% of the population over the age of 70 have symptoms of osteoarthritis.

There are several broad hypotheses on the cause of the disease. Genetic determinants of major histocompatibility complex (MHC-II) appear to be associated with arthritis. Environmental factors such as stress, viruses such as Epstein-Barr virus and parvo virus and collagen as an auto immunogen have also been mentioned as factors related to the development of arthritis. The disease appears to be initiated by the activation of T-cells. Inflammatory cytokines such as TNF-$\alpha$ are involved in the amplification of the disease process. Proliferation of endothelial cells in the rheumatoid synovium is an important component of inflammation in arthritis. The actual tissue damage is caused by the inflammatory cells such as PMNs and monocytes/macrophages. The damage is caused by the release of proteolytic and hydrolytic enzymes as well as toxic reactive oxygen radicals from these cells activated in the tissue and joints.

Therapy for arthritis involves alleviation of the symptoms associated with the disease, such as relief of pain, reduction of inflammation and increase of motion. Acetylsalicylic acid such as Aspirin, nonsteroid anti-inflammatory drugs such as ibuprofen, methotrexate and naproxen, and glucocorticoid have been used for the treatment of arthritis. Control of the symptoms with these drugs requires long term daily treatment. These drugs have a variety of toxic and other side effects, such as gastric erosion and adverse effects on kidneys and liver. Some of these drugs particularly glucocorticoid inhibit the immune response to infections. Therefore, there is a great need for alternative therapies for the management of arthritis which can eliminate the need for traditional drugs and their side effects particularly for prolonged daily use.

SUMMARY OF THE INVENTION

It is an object of the present invention to provide a formulation for the treatment of the symptoms associated with inflammation including arthritis.

It is an object of the present invention to provide a formulation for the prophylaxis of arthritic disease and inflammation.

It is a further object to provide a formulation based on a natural product which substantially avoids the side effects associated with traditional drugs used to alleviate symptoms associated with inflammation.

It is another object to provide a method for producing a formulation derived from rose-hip for the treatment of the symptoms associated with inflammation, including arthritis.

It is yet another object to provide a method for treating and/or alleviating the symptoms associated with inflammation including arthritis.

These and other objects of the present invention are achieved by a formulation comprising a rose-hip concentrate containing a high vitamin content relative to conventionally dried rose hip. In a preferred embodiment, the rose-hip concentrate comprises ground and dried rose hip, the rose hip dried at temperatures below 50° C., and in darkness to maintain the high vitamin content. The rose hip is formulated for oral administration, preferably in tablet or capsule form. One or multiple dose of the formulation may be administered totaling from about 20–200 g per day.

The inventors have discovered an anti-inflammatory property of rose-hip formulations, and that the use of the formulations, in a prophylactic and/or therapeutic regiment, prevents or alleviates and reduces symptoms associated with arthritis, such as rheumatoid arthritis, osteoarthritis, reactive arthritis and other forms of inflammation. Daily intake of rose-hip as described in this invention can replace or supplement conventional drug therapies and improve the quality of life in patients suffering form arthritis by relieving pain and improving motion in these patients.

DETAILED DESCRIPTION OF THE INVENTION

The present invention is directed to a formulation using rose-hip concentrate containing a high vitamin content. Rose-hip is harvested in a generally known manner when the hips are fully ripe. Hips from wild rose bushes, notably *rosa canina, rosa gallica, rosa condita* and *rosa rugosa*, may be used, but the hips of the *rosa canina* are particularly well suited to use in the invention.

After the hips are harvested, they are chopped into pieces. If further processing is delayed, the hips may be frozen for storage. In any event, the next step is to dry the chopped rose-hips to a water content of about 5% by weight. It is essential that the drying be conducted in an manner which preserves the vitamin content of the rose-hips. Preferably, drying is conducted at a temperature below 50° C., with air and avoiding sunlight. Such a powder has a high content of vitamin B, E and C, with about 560 mg. vitamin C per 100 g powder. It may be beneficial to utilize low pressure as well as low temperature to facilitate drying. Above 50° C., notable deterioration in vitamin content is possible.

The dried, chopped rose-hips then pass through a separation step to remove nuts, hairs, and other extraneous matter that may have accompanied the rose-hips during harvesting. The remaining fruit flesh is then crushed in a grinding mill. A powder or granular material may be obtained having a particle size of below 1 mm, with about 0.1 to 0.5 mm preferred. For ease in illustration, the term "powder" will be used to cover the full spectrum of the dried rose-hips in whatever solid form it takes. The powder may be referred to herein on occasion as "a concentrate" or as "an extract" and it will be understood, of course, that the powder may be presented and used as a solution, suspension or emulsion, and the invention is not limited to the solid form.

The powder may be packed in a conventional manner in bags, pelletized or placed directly into capsules with a physiologically acceptable carrier for formulation into unit dosages. An advantage of the rose-hip powder is that it may, without special processing, be incorporated into foods or beverages such as baked goods, non-baked goods, fruit and other beverages, etc. as well as be formulated with other dietary supplements such as vitamins, minerals, and other materials which may offer complimentary beneficial effects, such as anti-oxidants. This substantially simplifies the ability of a person suffering from inflammation including arthritis to obtain and maintain the amount necessary for the daily intake of the rose-hip powder to obtain beneficial results.

A unit dosage can comprise a therapeutically effective amount of the rose hip powder for a single daily administration (e.g., orally or by feeding tube in an enteral diet); or it can be formulated into smaller quantities to provide for multiple doses in a day. In either instance, the formulation of this invention can be manufactured into tablets, capsules, caplets, elixirs, enteral formulations or incorporated into slow-releasing carriers. Examples of physiologically acceptable vehicles including water, oil emulsions, alcohol or any of the food/beverage formulations described herein.

A unit dosage, as stated above, will depend upon many factors including age, condition and disease state of the patient and the number of times the unit will be taken in a single day. In any event, the entire daily dosage will be that which is physiologically acceptable to an individual and can be administered daily over a prolonged period of time.

A preferred unit dosage of the inventive powder will be from about 0.25 to about 2.0 g/kg/day. Thus, the total amount will likely be from about 20 to about 200 g/day, with about 40–120 g/day preferred.

Alternatively, the formulations can be incorporated within or used on many of the foods and beverages one can consume on a daily basis. Suitable foods and beverages which could be made, include but are not limited to, nutritional beverages, soft drinks, fruit beverages and juices, electrolyte containing beverages, puddings, baked goods (i.e., cookies, brownies, fudge, cake, breads), non-baked extruded foods (i.e., bars), salad dressings, condiments, confections (i.e., candy), snack foods (i.e., chips, pretzels, tortillas), drips and spreads, ice cream, frozen confections and novelties, dairy products such as yogurt, margarine-like spreads, seasonings such as for meat, poultry, seafood and salads. Fat free, reduced fat and low calorie versions of these foods are embraced by this invention. Incorporation of the formulation into foods/beverages provides the advantages of patient compliance over a prolonged period of use and in a form which is more desirable to the consumer, rather than in the form of a medicament.

The powder of the invention has various vitamins and minerals as determined according to conventional methods. These are shown in the following Table 1.

TABLE 1

| Analyze (per 400 g) | Result |
| --- | --- |
| Vitamin A | <10 µg/100 g |
| Vitamin B1 | <0.2 mg/100 g |
| Vitamin B2 | 0.99 mg/100 g |
| Vitamin B6 | 0.20 mg/100 g |
| Vitamin B12 | <0.5 µg/100 g |
| Vitamin C | 560 mg/100 g |
| Vitamin K1 | 63 µg/100 g |
| Vitamin E | 4.6 mg/100 g |
| Niacin | 0.96 mg/100 g |
| Calcium | 630 mg/100 g |
| Phosphorus | 160 mg/100 g |
| Magnesium | 170 mg/100 g |
| Iron | 1.9 mg/100 g |
| Potassium | 0.97% |
| Sodium | 0.018% |
| Sulphur | 1000 mg/kg |
| Zinc | 1,0 mg/100 g |
| Copper | 10,900 µg/100 g |
| Manganese | 3,900 µg/100 g |
| Silicon | 85 mg/kg |
| Iodine | 93 µg/100 g |
| Selenium total | <0.020 mg/kg |
| Chromium | <0.020 mg/kg |
| Molybdenum | 0.21 mg/kg |
| Cobalt | <0.050 mg/kg |
| Nickel | 0.79 mg/kg |
| Aluminum | 8.7 mg/kg |
| Boron | 15 mg/kg |
| Fluorine | 2 mg/kg |

TABLE 1-continued

| Analyze (per 400 g) | Result |
|---|---|
| Chloride | 0.5 g/kg |
| Lithium | 0.041 mg/kg |

Analysis of Contents.

As shown in Table I, the inventive rose-hip powder contains several vitamins such as vitamin A, vitamin B, vitamin C, vitamin E and vitamin K, as well as several minerals. This powder can be obtained from Hyben Vital, Tranekaer, Denmark, the assignee of the present invention, the product known as HYBEN VITAL™ rose-hip powder.

Uptake Through Gastro-intestinal Tract.

45 g of the inventive powder having an equivalent of 250 mg of vitamin C was administered to healthy volunteers by oral intake with 500 mg of vitamin C given to a control group. The concentration of vitamin C in blood was measured at 0, 5, 10, 15, 20 and 25 hours following intake. In another study different amounts of the inventive powder were administered to six healthy volunteers and the concentration of vitamin C in blood was measured at 0, 2 and 4 hours following intake.

Preparation of Rose-hip Extract.

20 mg/ml of rose-hip powder was mixed with 4 ml of minimal essential medium (MEM) and incubated for 19 hours at 5° C. Following incubation the mixture was centrifuged at 4000 rpm for 10 min. The supernatant was collected and diluted further for the leukocyte function assays.

Polymorphonuclear Leukocytes and Monocytes.

Polymorphonuclear leukocytes (PMNs) and mononuclear leukocytes containing monocytes were isolated from the peripheral blood of healthy individuals in citrated glass. The cells were separated by dextran density gradient and lymphoprep separation. The purity of PMNs was greater than 98% and the cell viability as determined by trypan blue dye exclusion was greater than 98%. The percentages of monocytes in the mononuclear cell fraction was between 15%–35% and the cell viability was greater than 98%.

Chemotaxis.

Chemotaxis assay was performed using a modified Boyden chamber technique as previously described in Jensen, P., and Kharazmi, A., Computer-assisted image analysis assay of human neutrophil Chemotaxis in vitro. J. Immunol. Methods. 144:43. 1991. The purified PMNs or mononuclear cells were preincubated with different dilutions of rose-hip extract for 30 min at 37° C. Following preincubation the chemotaxis of the cells towards the chemotactic peptide f-Met-Leu-Phe (fMLP) or zymosan activated serum (ZAS) which contains the biologically active chemoattractant C5a were tested. The migrated cells were counted by a computer-assisted image analysis system.

Chemiluminescence.

Chemiluminescence assay was used as a measure of oxygen radical generation by activated PMNs. The method was performed as previously described in Kharazml, A., Hoiby, N., Doring, G., and Valerius, N. H. *Pseudomonas aeruginosa* exoproteases inhibit human neutrophil chemiluminescence. Infect. Immun. 44:587, 1984. PMNs were preincubated with different concentrations of the inventive rose-hip extract and then stimulated with either fMLP or opsonized zymosan. The oxidative burst response of the activated cells was measured by a 1250 LKB Wallace luminometer.

In Vivo Studies.

Subjects.

Eighteen healthy volunteers represented by both sexes with a mean age of 48 years, range 30–62 years were included in this study. One of the volunteers left the study after three days of therapy, as he could not change his job schedule and be present on the days of blood sampling leaving 17 volunteers for the study. All the subjects included were without known cardiovascular, immunological, kidney, liver, allergic, rheumatological or haernatological disorders. Three of the subjects, all men, suffered from mild osteoarthritis, for which medication was not taken.

Design of the in Vivo Study.

The volunteers were treated with 45 grams of the inventive rose-hip powder daily for 28 days, and followed for another 28 days during which rose-hip powder was not taken. Before inclusion, all volunteers went through a screening procedure to assure that non of the above mentioned diseases were present. Moreover before inclusion blood samples were taken for C-reactive protein (CRP) measurement to assure that none of the included volunteers suffered from unknown infectious diseases. Furthermore blood potassium, sodium, serum creatinine, alanine-amino transferase, alkaline phosphatase, lactate dehydrogenase, bilirubin, hemoglobin and total cholesterol were also measured before initiation of the treatment. All measurements were performed according to the conventional laboratory routine. All the above mentioned parameters except serum creatinine and CRP were repeated after 5, 10, 21 and 28 days of therapy, and again 28 days after stopping rose-hip therapy. Serum creatinine and C-reactive protein (CRP) were tested before therapy, after 10 and 28 days of therapy and finally 28 days following cessation of the treatment. Rose-hip was taken together with a meal at 12.00 AM. On the days of blood sampling, the rose-hip powder was taken together with a light meal at 9.00 AM, two hours before blood sampling. Blood sampling was always performed after 15 minutes at rest sitting in a chair. After 28 days of rose-hip therapy blood samples were collected in special test tubes and analyzed for polymorphonuclear leucocyte chemotaxis using a Boyden chamber technique as described earlier. PMN chemotaxis was then compared to values obtained in a period where the volunteers had not taken any rose-hip the proceeding 28 days.

Statistical Analysis.

Statistical analysis of the data was performed by using a Wilcoxon test for matched pairs. P values of less than 0.05 were considered significant.

RESULTS

Uptake Through Gastro-intestinal Tract.

Figure 1:
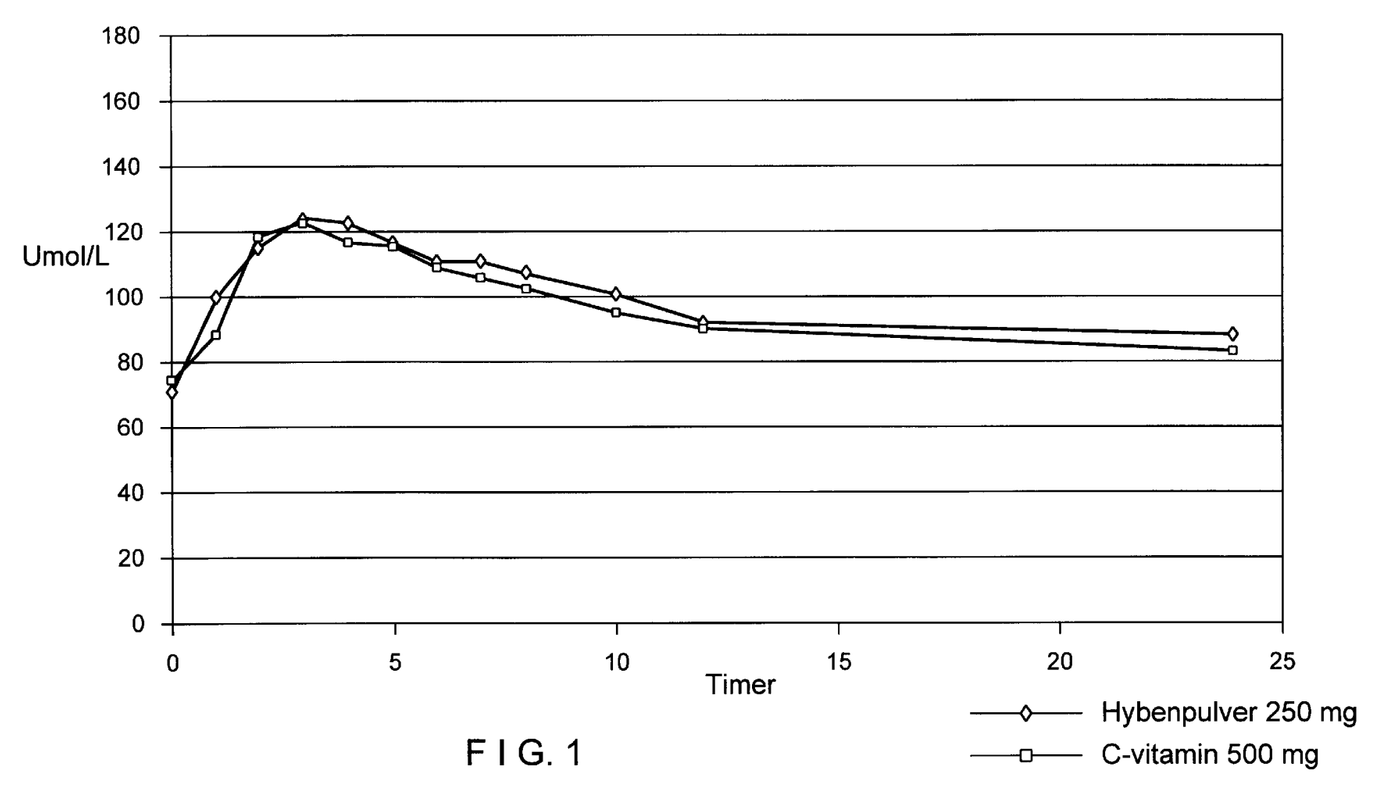
FIG. 1 is a graph showing the uptake of vitamin C present in rose-hip powder administered to healthy volunteers. An amount of rose hip powder having an equivalent of 250 mg of vitamin C present in about 45 g of rose hip powder was administered by oral intake to healthy volunteers and the blood level of vitamin C was measured at different time points. The powder was swallowed and washed down with water. 500 mg of commercially available vitamin C in tablet form was administered to control subjects.

As shown in FIG. I the uptake of vitamin C present in the inventive powder was as good or even better than uptake of vitamin C when given in tablet form. The concentrations and kinetics of uptake through gastro-intestinal tract of equivalent of 250 mg vitamin C in the inventive rose-hip powder was similar to 500 mg vitamin C in tablet form. The better absorption of vitamin C in rose-hip powder could be due to a larger surface area of rose-hip powders as compared to vitamin C tablets.

Chemotaxis.

The effect of rose-hip extract on human peripheral blood polymorphonuclear leucocyte (PMN) chemotaxis response as measured by a modified Boyden chamber assay are shown in Table 2. Rose-hip extract was prepared by incubating the rose-hip powder in MEM for 19 hours at 5° C. After incubation the preparation was centrifuged at 4000 rpm for 10 min and the supernatant was diluted in MEM in appropriate concentrations. The cells were preincubated with different concentrations of the extract for 30 minutes at 37° C. After preincubation, chemotaxis of the cells towards the chemotactic peptide fMLP or zymosan activated serum (ZAS) which contains C5a was determined. The data are from two representative experiments performed in triplicate and presented as percent inhibition of chemotaxis as compared to control cell response preincubated with buffer alone.

TABLE 2

| Rose-hip extract Concs ($\mu$g/ml) | fMLP | ZAS |
|---|---|---|
| Experiment 1 | | |
| 5000 (pH 4.62) | 98 | 100 |
| 2500 (pH 5.33) | 95 | 100 |
| 1000 (pH 6.39) | 69 | 94 |
| 500 (pH 6.76) | 49 | 92 |
| 100 (pH 7.06) | 25 | 64 |
| Experiment 2 | | |
| 5000 (pH 4.66) | 100 | 100 |
| 5000 (pH 7.2) | 100 | 98 |
| 2500 (pH 5.41) | 100 | 100 |
| 2500 (pH 7.2) | 99 | 100 |
| 1000 (pH 6.47) | 93 | 100 |
| 1000 (pH 7.2) | 93 | 100 |

As shown in Table 2 rose-hip extract at concentrations as low as 100 $\mu$g/ml inhibited the chemotaxis of human peripheral blood neutrophils. At concentrations higher than 100 $\mu$g/ml inhibition of chemotaxis was 100%. pH-adjusted rose-hip extract at concentrations of 100 $\mu$g/ml and higher was as strongly inhibitory as the non-pH-adjusted rose-hip extract.

Effect of rose-hip extract on human peripheral blood mononuclear leukocyte (PBMC) chemotaxis response as measured by a modified Boyden chamber assay is shown in Table 3. Rose-hip extract was prepared by incubating rose-hip powder in MEM for 19 hours at 5°' C. After incubation, the preparation was centrifuged at 4000 rpm for 10 min and the supernatant was diluted in MEM in appropriate concentrations. The pH of the rose-hip extract was adjusted to pH 7.0. The cells were preincubated with different concentrations of the extract for 30 minutes at 37° C. After preincubation chemotaxis of the cells towards the chemotactic peptide fMLP or zymosan activated serum (ZAS) which contains C5a was determined. The data are from one representative experiment performed in triplicate and presented as percent inhibition of chemotaxis as compared to control cell response preincubated with buffer alone.

TABLE 3

| Rose-hip extract Concs ($\mu$g/ml) | fMLP | ZAS |
|---|---|---|
| 2000 | 90 | 85 |
| 1000 | 94 | 95 |
| 500 | 77 | 90 |

Table 3 shows the chemotaxis results of peripheral blood monocytes incubated with rose hip extract. Rose-hip extract at concentrations of 500 $\mu$g/ml inhibited the chemotaxis of human monocytes by about 80–90%.

Chemiluminescence.

The effect of rose-hip extract on human peripheral blood polymorphonuclear leucocyte (PMN) chemiluminescence response as measured by an LKB luminometer is shown in Table 4. Rose-hip extract was prepared by incubating rose-hip powder in MEM for 19 hours at 5° C. After incubation the preparation was centrifuged at 4000 rpm for 10 min and the supernatant was diluted in MEM in appropriate concentrations. The cells were preincubated with different concentrations of rose-hip extract for 30 minutes at 37° C. After preincubation the chemiluminescence response of cells activated by opsonized zymosan was determined. The data are from three experiments performed in duplicate and are presented as percent inhibition of chemiluminescence as compared to control cell response preincubated with buffer alone.

TABLE 4

| Rose-hip extract Concs ($\mu$g/ml) | Experiment 1 | Experiment 2 | Experiment 3 |
|---|---|---|---|
| 5000 | 71 | 46 | 68 |
| 2500 | 37 | 27 | 57 |
| 1000 | 8 | 8 | 12 |
| 500 | 0 | 0 | ND |
| 100 | 0 | 0 | 0 |
| 50 | 0 | ND | ND |

ND: Not determined.

As shown in Table 4, rose-hip extract inhibited the chemiluminescence of activated by opsonized zymosan. Adjustment of pH to physiological values in act did not influence the inhibitory effect markedly.

Vitamin C.

Vitamin C was used as a control. Vitamin C in crystalline form up to a concentration of 5000 $\mu$g/ml had almost no effect on PMN chemiluminescence when the pH of vitamin C solution was adjusted to the physiological pH 7.2.

Vitamin E.

Vitamin E (alpha-tocopherol) was also used as a known anti-oxidant control. Vitamin E at a concentration of over 1 $\mu$g/ml inhibited chemiluminescence.

Patient Studies.

Blood Chemistry.

Blood levels of potassium, sodium, alanine-amino transferase (AL/AT), alkaline phosphatase, lactate dehydrogenase (LDH), billrubin and total cholesterol from before treatment and on days of 10 and 28 during treatment and 34 days after treatment as shown in table 5. The data are presented as mean values from 17 subjects.

TABLE 5

| | Day 0 | Day 10 | Day 28 | Day 62 |
|---|---|---|---|---|
| Potassium (mmol/L) | 4.11 | 4.08 | 4.21 | 4.13 |
| Sodium (mmol/L) | 138.2 | 137.5 | 139.1 | 141.8 |
| AL/AT (Units/L) | 19.18 | 18.12 | 18.71 | 16.56 |
| Alkaline phosphatase (Units/L) | 162.7 | 150.7 | 158.2 | 159.1 |
| LDH (Units/L) | 318.8 | 303.7 | 312.4 | 327.3 |
| Bilirubin ($\mu$mol/L) | 9.41 | 8.00 | 8.29 | 9.43 |
| Cholesterol (mmol/L) | 6.20 | 6.04 | 6.05 | 6.25 |

As shown in Table 5, no significant changes occurred in potassium, sodium, alanine-amino transferase, alkaline phosphatase, lactate dehydrogenase, billrubin, hemoglobin and total cholesterol comparing values from before therapy to values obtained after 5, 10, 21 and 28 days of therapy and values obtained 28 days after stopping therapy. Serum creatinine, however, declined significantly as compared to initial values (92.00±82 $\mu$mol/l) to values obtained after 10 days (88.63±80.5) and 28 days (86.47±81.32) of therapy, respectively (p<0.001). When treatment had been stopped for 28 days the serum creatinine levels significantly increased (95.56±81.20) (p<0.001) and were similar to values obtained before therapy.

Concentrations of C-reactive protein in different individuals before (day 0), during (day 10 and day 28) and after treatment (day 62) with 45 grams daily intake of rose-hip for 28 days as shown in Table 6. The results are given as mg/L CRP.

TABLE 6

| Subjects | Day 0 | Day 10 | Day 28 | Day 62 |
|---|---|---|---|---|
| 1 | 6 | 3 | 4 | 5 |
| 2 | 6 | 5 | 7 | 6 |
| 3 | 5 | 2 | 5 | 6 |
| 4 | 4 | 2 | 4 | 5 |
| 5 | 4 | 6 | 3 | 3 |
| 6 | 9 | 8 | 10 | 16 |
| 7 | 7 | 6 | 4 | 10 |
| 8 | 5 | 3 | 8 | 5 |
| 9 | 5 | 9 | 5 | 6 |
| 10 | 3 | 6 | 3 | 5 |
| 11 | 6 | 3 | 3 | 4 |
| 12 | 4 | 1 | 4 | 4 |
| 13 | 5 | 4 | 4 | 5 |
| 14 | 9 | 4 | 4 | 7 |
| 15 | 5 | 1 | 2 | 6 |
| 16 | 5 | 4 | 3 | 8 |
| Mean | 5.50 | 4.19 | 4.56 | 6.31 |
| ±SD | 1.67 | 2.34 | 2.10 | 3.07 |

Figure 2:
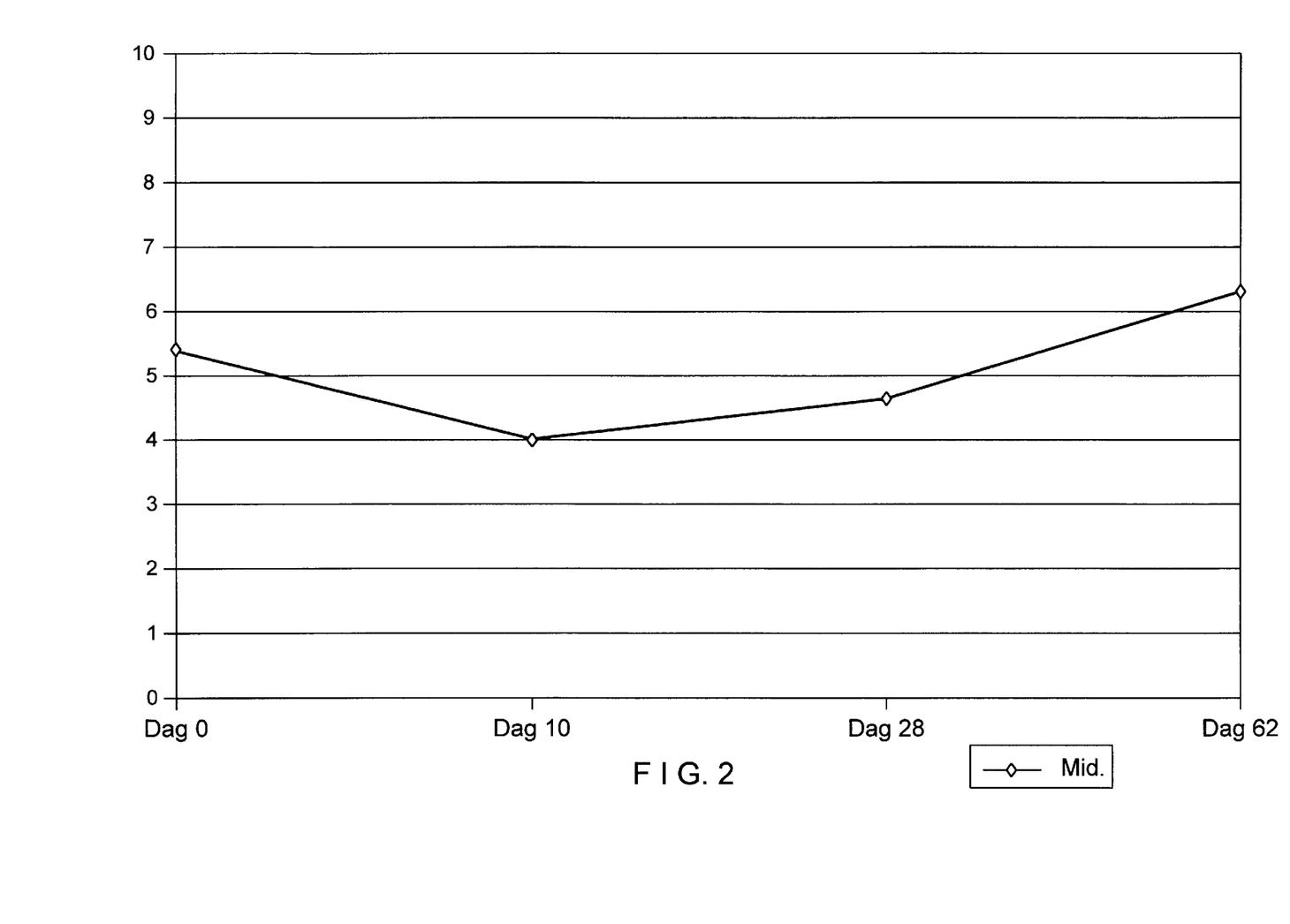
FIG. 2 is a graph showing the blood levels of C-reactive protein (CRP) in individuals before (day 0), during (day 10 and day 28) and after treatment (day 62) with 45 grams daily intake of rose-hip for 28 days. The results are given as mean values and in mg/L CRP.

The data on C-reactive protein are shown in Table 6 and FIG. 2. These results were similar to those obtained when evaluating serum creatinine. The initial mean level of CRP was 5.50±1.67 declined to 4.18±2.34 and 4.56±2.09 mg/L, after 10 and 28 days of therapy respectively ($p<0.05$). After stopping therapy for 28 days the level increased to 6.31±3.07 mg/L ($p<0.02$) compared to previous time point.

Polymorphonuclear Leukocyte Chemotaxis.

Chemotaxis of peripheral blood polymorphonuclear leukocytes from subjects during and 28 days after cessation of treatment with 45 grams daily intake of rose-hip for 28 days are shown in Table 7. The chemotaxis is determined towards the chemotactic peptide fMLP and zymosan activated serum (ZAS) as shown in Table 7. The results are given as number of cells migrated.

TABLE 7

| Subjects | fMLP | | ZAS | |
|---|---|---|---|---|
| | During | After | During | After |
| 1 | 352 | 338 | 389 | 336 |
| 2 | 180 | 299 | 419 | 612 |
| 3 | 234 | 420 | 642 | 743 |
| 4 | 181 | 331 | 548 | 730 |
| 5 | 389 | 468 | 645 | 752 |
| 6 | 289 | 377 | 534 | 661 |
| 7 | 25 | 355 | 81 | 561 |
| 8 | 3 | 397 | 36 | 687 |
| 9 | 214 | 257 | 462 | 611 |
| 10 | 11 | 427 | 20 | 679 |
| 11 | 6 | 299 | 33 | 536 |
| 12 | 6 | 290 | 44 | 535 |
| 13 | 38 | 106 | 132 | 483 |
| 14 | 21 | 250 | 43 | 500 |
| 15 | 55 | 262 | 87 | 496 |
| 16 | 25 | 297 | 76 | 282 |
| 17 | 66 | 175 | 309 | 378 |
| Mean | 123 | 315 | 265 | 564 |
| ±SD | 131 | 92 | 238 | 141 |

Figure 3:
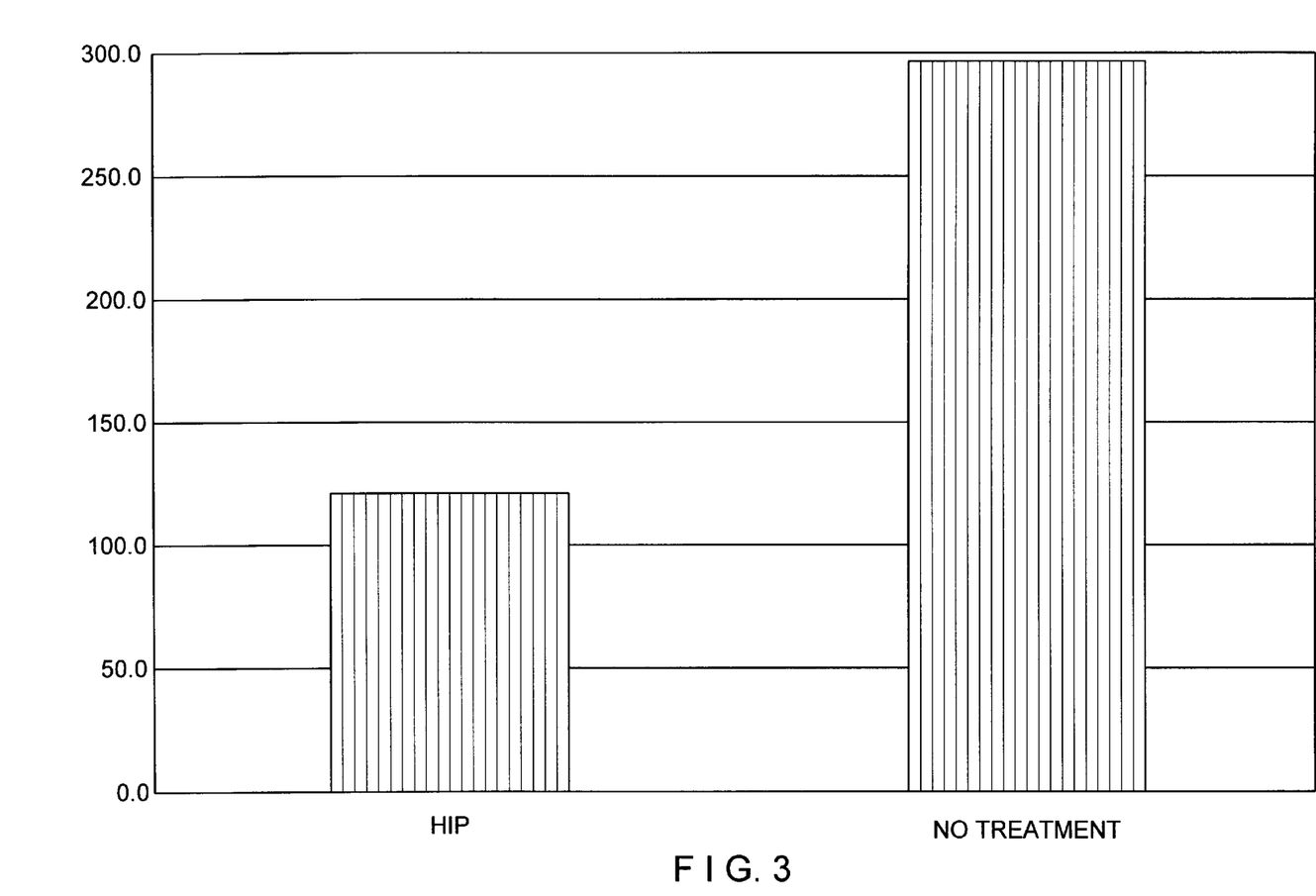
FIG. 3 is a graph showing the chemotaxis of peripheral blood polymorphonuclear leukocytes from subjects during and 28 days after cessation of treatment with 45 grams daily intake of rose-hip for 28 days. The chemotaxis is determined towards the chemotactic peptide fMLP. The results are given as mean number of cells migrated from 17 subjects.
Figure 4:
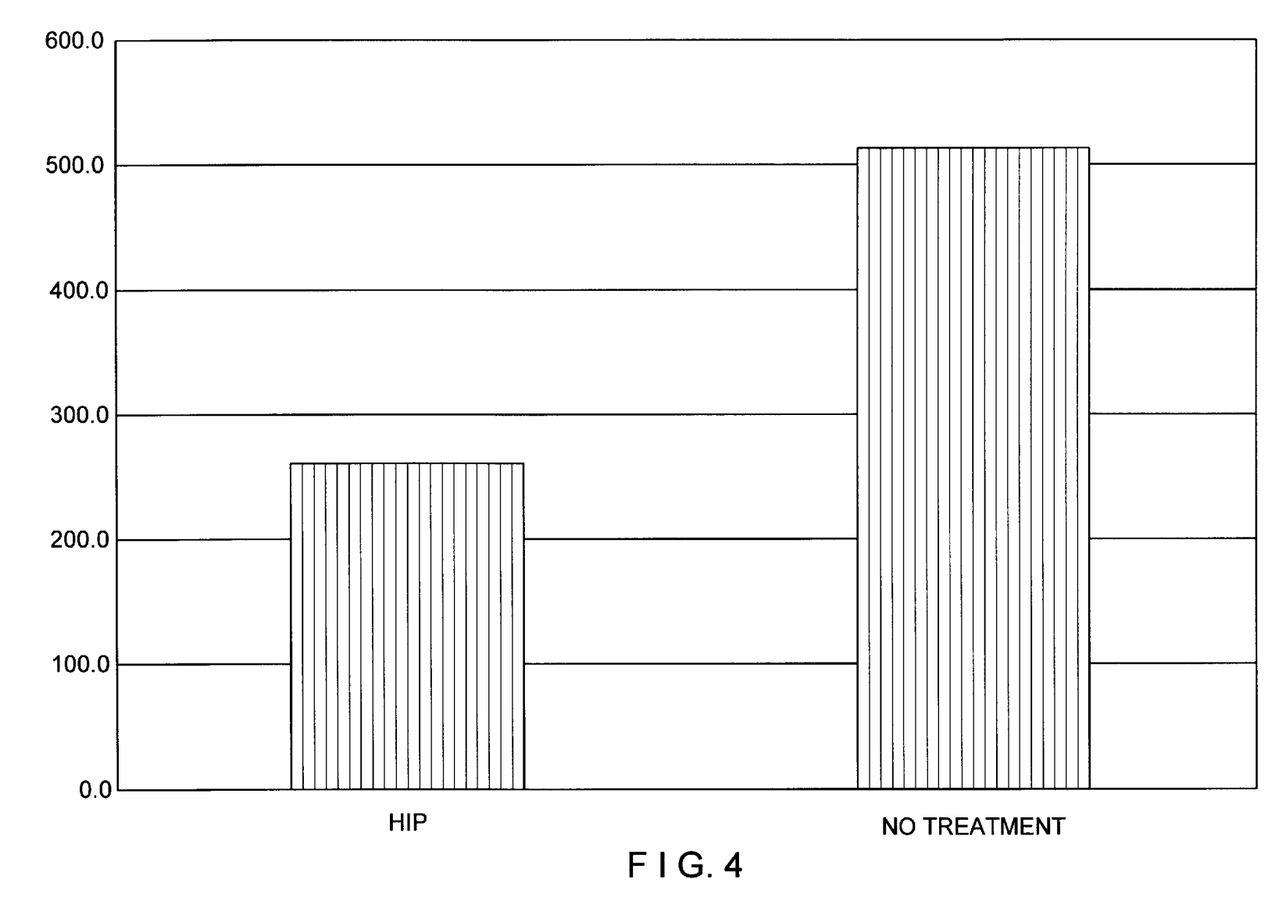
FIG. 4 is a graph showing the chemotaxis of peripheral blood polymorphonuclear leukocytes from subjects during and 28 days after cessation of treatment with 45 grams daily intake of rose-hip for 28 days. The chemotaxis is determined towards zymosan activated serum (ZAS). The results are given as mean number of cells migrated from 17 subjects.

The data is shown in Table 7 and FIGS. 3 and 4. The mean value of PMN chemotaxis towards the chemotactic peptide fMLP was 123±131 when tested on 28th day of treatment with rose-hip as compared to 315±92 when blood samples were taken 28 days after cessation of treatment with rose-hip ($p<0.001$). The mean PMN chemotaxis towards zymosan treatment with activated serum (ZAS) which contains the biologically active chemotactic factor C5a was 265±288 as compared to 564±141 when tested 28 days after cessation of treatment with rose hip ($p<0.001$).

The decline in chemotaxis response to fMLP was 67%, a considerable decline of chemotaxis response in 16 out of 17 volunteers. The decline in chemotaxis response to ZAS was 53%, also a considerable decline in 16 out of 17 volunteers. It was the same volunteer who did not respond to therapy in both assays.

Clinical Findings.

The three volunteers, who complained of mild pain of osteoarthritis origin reported that their pain declined after 14 days of rose-hip therapy. In all three cases the pain returned 12–14 days after stopping therapy. Six volunteers reported that they slept better during the night while on rose-hip therapy. They also reported that they no longer needed to visit a toilet during the night while on rose-hip therapy. No allergic reactions were observed during therapy, but two volunteers complained of mild gastrointestinal air disturbances at the end of the study.

Conclusions.

In conclusion, the studies described demonstrate that the rose-hip extract inhibited, in vitro, the chemotaxis and oxidative burst response of the human peripheral blood polymorphonuclear leukocytes, the most important and most abundant inflammatory cells. The extract also inhibited/reduced the chemotaxis of monocytes, another important cell type involved in inflammation and in pathogenesis of arthritis. It appears that the inhibition of neutrophil chemotaxis and oxidative burst response by rose-hip extract was not due to vitamin C content of the extract. This is shown by the inability of pH-adjusted vitamin C to inhibit chemiluminescence whereas pH-adjusted extract was still as inhibitory as non-pH-adjusted extract. The anti-inflammatory and anti-oxidant properties of rose-hip are important in the inhibition and/or reduction of tissue damage in the inflamed joint. Furthermore, administration of rose hip to patients with arthritis resulted in alleviating pain and reducing inflammation and other symptoms associated with arthritis. Rose-hip administered at a dose of 45 grams daily to healthy volunteers for a period of 28 days, inhibited the chemotaxis response of polymorphonuclear leucocytes by approximately 50%. Moreover rose-hip lowered the level of the acute phase protein C-reactive protein in volunteers with values within normal range, which is below 10 mg/L. This decline was significant and was observed after 10 days of therapy. Alleviation/reduction of physical symptoms by rose-hip correlated very well with the reduced chemotaxis of peripheral blood neutrophils and reduced level of C-reactive protein in the subjects under therapy. After the patients stopped taking rose-hip powder the chemotaxis of neutrophils and the levels of C-reactive protein were increased to untreated values. The blood chemistry data presented in this invention show that intake of rose-hip had no harmful effect on any of the liver and kidney function parameters performed in this study.

Although the focus of the invention discussed above is for human therapy, it is also contemplated to use the herbal formulation of this invention as a therapeutic or prophylactic for non-human mammals, including domestic and farm animals, having arthritis or other T cell mediated immune disease for which it is desirable to reduce/suppress immune response or alleviate joint pain and stiffness caused by these diseases. The skilled artisan would readily ascertain the mode and method of therapy based upon the animal to be treated. For example, the formulation can be incorporated into the animal's water source or feed, or it can be administered like a medicament in the form of a capsule, tablet, liquid or the like.

The drugs presently available for the therapy of arthritis include acetylsalicylic acid such as Aspirin, non-steroid anti-inflammatory drugs such as ibuprofen, methotrexate and naproxen, and glucocorticoid. Control of the symptoms with these drugs requires long term daily treatment. These drugs have a variety of toxic and other side effects, such as gastric erosion and adverse effects on kidneys and liver. Some of these drugs particularly glucocorticoid inhibit the immune response to infections. Therefore, there is a great need for alternative therapies for the management of arthritis which can eliminate the need for traditional drugs and their side effects particularly for prolonged daily use. The inventive rose-hip powder possesses these properties, in that it is effective, safe and cheap. As a natural product, it has no side effects. It can be administered by itself alone as capsules, tablets, powder, tea or other preparations. Rose-hips in powder form or as an extract of rose-hip can also be used as an ingredient incorporated into suitable foods or beverages, without special processing requirements, including but not limited to, baked goods, confections, frozen confections, puddings, snack foods, salad dressings, nutritional beverages, soft drinks, fruit beverages, dips and spreads, ice cream, dairy products such as yogurt, margarine-like spreads, seasonings such as for meat, poultry, seafoods and salads, and nonbaked foods. The inventive rose-hip powder can also be used in combination with other dietary supplements such as vitamins, minerals and anti-oxidants. Preparations containing rose-hip can be designed for daily consumption as part of therapeutic regimen for arthritis, or as a prophylactic regimen for individuals having a genetic or environmental predisposition to arthritis.

While preferred embodiment of the present invention has been shown and described, it will be understood by those skilled in the art that various changes or modifications can be made without varying from the spirit and scope of the present invention, and the invention is not limited to the examples given.

What is claimed is:

1. A formulation comprising a rose hip concentrate containing a high vitamin content of vitamin C per gram of concentrate, the concentrate further containing vitamin A, vitamin $B_2$, vitamin $B_6$, vitamin $B_{12}$, vitamin $K_1$ and vitamin E.

2. The formulation of claim 1 further comprising a physiologically acceptable carrier.

3. The formulation of claim 1 wherein the concentrate is a powder having a water content of about 5% by weight.

4. The formulation of claim 1 wherein the formulation is in a unit dosage form.

5. The formulation of claim 1 wherein the rose hip concentrate is obtained from *rosa canina*.

6. A method for alleviating the symptoms associated with inflammation in a mammal by inhibiting chemotaxis and oxidative burst response of peripheral blood neutrophils comprising:

providing a formulation having a rose hip concentrate containing a high vitamin content of vitamin C per gram of concentrate, vitamin A, vitamin $B_2$, vitamin $B_6$, vitamin $B_{12}$, vitamin $K_1$ and vitamin E in a physiologically acceptable form; and administering a therapeutically effective amount of the formulation to the mammal.

7. A method for preventing inflammation in a mammal by inhibiting chemotaxis and oxidative burst response of peripheral blood neutrophils comprising:

providing a formulation having a rose hip concentrate containing a high vitamin content of vitamin C per gram of concentrate, vitamin A, vitamin $B_2$, vitamin $B_6$, vitamin $B_{12}$, vitamin $K_1$ and vitamin E in a physiologically acceptable form; and administering a prophylactically effective amount of the formulation to the mammal.

8. The method of claim 5 wherein the rose hip concentrate is a powder.

9. The method of claim 5 wherein the rose hip concentrate is a powder having a water content of about 5% by weight.

10. The method of claim 5 wherein the formulation is administered at from about 20 to about 200 g/day, in unitary or multiple doses.

11. The method of claim 5 wherein the formulation is administered at from about 0.5 to about 2 g/kg body weight per day.

12. The method of claim 5 wherein the mammal is a human.

13. A method for relieving pain and inflammation associated with arthritis in a mammal comprising:

providing a formulation having a rose hip concentrate having a high vitamin content of vitamin C per gram of concentrate, vitamin A, vitamin $B_2$, vitamin $B_6$, vitamin $B_{12}$, vitamin $K_1$, and vitamin E in a physiologically acceptable form; and administering a therapeutically effective amount of the formulation to the mammal.

14. A method for preventing arthritis in a mammal by inhibiting chemotaxis and oxidative burst response of peripheral blood neutrophils and reducing a level of c-reactive protein comprising:

providing a formulation having a rose hip concentrate having a high vitamin content of vitamin C per gram of concentrate, vitamin A, vitamin $B_2$, vitamin $B_6$, vitamin $B_{12}$, vitamin $K_1$ and vitamin E in a physiologically acceptable form; and administering a therapeutically effective amount of the formulation to the mammal.

15. The method of claim 13 wherein the rose hip concentrate is a powder having a high vitamin content.

16. The method of claim 13 wherein the rose hip concentrate is a powder having a water content of about 5% by weight.

17. The method of claim 13 wherein the formulation is administered at from about 20 to about 200 g/day, in unitary or multiple doses.

18. The method of claim 13 wherein the formulation is administered at from about 0.5 to about 2 g/kg body weight per day.

19. The method of claim 13 wherein the mammal is a human.

20. A method for producing a formulation containing a rose hip concentrate having a high vitamin content of vitamin C per gram of concentrate, vitamin A, vitamin $B_2$, vitamin $B_6$, vitamin $B_{12}$, vitamin $K_1$ and vitamin E comprising:

obtaining a plurality of rose hips;

fracturing the rose hips into pieces;

separating a flesh portion of the rose hips from other matter;

drying the flesh portion of the rose hips at temperatures below 50° C., to a water content of about 5%;

grinding the dried flesh portion of the rose hips to produce a powder; and, providing the powder in a physiologically acceptable form.

21. The method of claim 20 further comprising, after the fracturing step, freezing the rose hip pieces for storage prior to the separating step.

22. A food or beverage containing the formulation of claim 1.

* * * * *